(12) United States Patent
Sisken (10) Patent No.: US 8,414,633 B2
(45) Date of Patent: Apr. 9, 2013

(54) STENT DELIVERY SYSTEM WITH A RETENTION WIRE

(75) Inventor: Richard B. Sisken, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1777 days.

(21) Appl. No.: 11/488,331

(22) Filed: Jul. 18, 2006

(65) Prior Publication Data

US 2007/0021820 A1     Jan. 25, 2007

Related U.S. Application Data

(60) Provisional application No. 60/701,310, filed on Jul. 21, 2005.

(51) Int. Cl.
*A61F 2/06* (2006.01)
(52) U.S. Cl. .................................................. 623/1.11
(58) Field of Classification Search ................ 623/1.11; 606/192, 194, 108
See application file for complete search history.

(56) References Cited

U.S. PATENT DOCUMENTS

| 4,913,141 | A  | * | 4/1990  | Hillstead ........................ 623/1.11 |
| 6,007,545 | A  | * | 12/1999 | Venturelli ....................... 606/108 |
| 6,142,926 | A  | * | 11/2000 | Schneiderman ................... 600/3 |
| 6,183,481 | B1 | * | 2/2001  | Lee et al. ....................... 606/108 |
| 2003/0050684 | A1 | * | 3/2003 | Abrams et al. ................. 623/1.11 |
| 2005/0154440 | A1 | * | 7/2005 | Limon .......................... 623/1.11 |
| 2005/0288764 | A1 | * | 12/2005 | Snow et al. .................... 623/1.11 |
| 2006/0064036 | A1 | * | 3/2006 | Osborne et al. ................. 600/585 |
| 2006/0086440 | A1 | * | 4/2006 | Boylan et al. .................. 148/563 |
| 2007/0010762 | A1 | * | 1/2007 | Ressemann et al. ............. 600/585 |

\* cited by examiner

*Primary Examiner* — Gary Jackson
*Assistant Examiner* — Jonathan Hollm
(74) *Attorney, Agent, or Firm* — Brinks Hofer Gilson and Lione (57) ABSTRACT

A delivery system is provided with a balloon catheter having a stent mounted thereon. A retention wire is provided to restrain the stent on the balloon of the balloon catheter. The retention wire is coupled to the catheter adjacent the distal end of the stent and adjacent the proximal end of the stent. The retention wire extends along the length of the stent adjacent the outer surface thereof. Thus, the retention wire may restrain the stent from moving longitudinally during inflation of the balloon.

18 Claims, 2 Drawing Sheets

STENT DELIVERY SYSTEM WITH A RETENTION WIRE

This application claims priority to U.S. Provisional Application No. 60/701,310, filed Jul. 21, 2005, which is hereby incorporated by reference herein.

BACKGROUND

The present invention relates generally to medical devices and more particularly to balloon catheters with a stent mounted thereon.

Stents have become a relatively common medical device for treating a number of organs, such as the vascular system, colon, biliary tract, urinary tract, esophagus, trachea and the like. Stents are useful in a variety of medical procedures and are often used to treat blockages, occlusions, narrowing ailments and other related problems that restrict flow through a passageway. Stents are also useful in treating other ailments including various types of aneurysms and may be useful in numerous other medical procedures as well.

Although stents are used in many different procedures, one common medical procedure in which stents are used involves implanting an endovascular stent into the vascular system. Stents have been shown to be useful in treating numerous vessels throughout the vascular system, including coronary arteries, peripheral arteries (e.g., carotid, brachial, renal, iliac and femoral), and other vessels. However, the use of stents in coronary arteries has drawn particular attention from the medical community because of the growing number of people suffering from heart problems associated with stenosis (i.e., a narrowing of an arterial lumen). This has lead to an increased demand for medical procedures to treat stenosis of the coronary arteries. In addition, the medical community has adapted many intravascular coronary procedures to other intraluminal disorders. The widespread frequency of heart problems may be due to a number of societal changes, including the tendency of people to exercise less while eating greater quantities of unhealthy foods, in conjunction with the fact that people generally now have longer life spans than previous generations. Stents have become a popular alternative for treating coronary stenosis because stenting procedures are considerably less invasive than other alternatives. Traditionally, stenosis of the coronary arteries has been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient.

Many different types of stents and stenting procedures are possible. In general, however, stents are typically designed as tubular support structures that may be inserted percutaneously and transluminally through a body passageway. Typically, stents are made from a metallic or other synthetic material with a series of radial openings extending through the support structure of the stent to facilitate compression and expansion of the stent. However, other types of stents are designed to have a fixed diameter and are not generally compressible. Although stents may be made from many types of materials, including non-metallic materials and natural tissues, common examples of metallic materials that may be used to make stents include stainless steel, nitinol, cobalt-chrome alloys, amorphous metals, tantalum, platinum, gold, magnesium and titanium. Typically, stents are implanted within an artery or other passageway by positioning the stent within the lumen to be treated and then expanding the stent from a compressed diameter to an expanded diameter. The ability of the stent to expand from a compressed diameter makes it possible to thread the stent through narrow, tortuous passageways to the area to be treated while the stent is in a relatively small, compressed diameter. Once the stent has been positioned and expanded at the area to be treated, the tubular support structure of the stent contacts and radially supports the inner wall of the passageway. As a result, the implanted stent mechanically prevents the passageway from closing and keeps the passageway open to facilitate fluid flow through the passageway. However, this is only one example of how a stent may be used, and stents may be used for other purposes as well.

Particular stent designs and implantation procedures vary widely. For example, stents are often generally characterized as either balloon-expandable or self-expandable. However, the uses for balloon-expandable and self-expandable stents frequently overlap and procedures related to one type of stent are frequently adapted to other types of stents.

Balloon-expandable stents are frequently used to treat stenosis of the coronary arteries. Usually, balloon-expandable stents are made from ductile materials that plastically deform relatively easily. In the case of stents made from metal, 316L stainless steel which has been annealed is a common choice for this type of stent. One procedure for implanting balloon-expandable stents involves mounting the stent circumferentially on the balloon of a balloon-tipped catheter and threading the catheter through a vessel passageway to the area to be treated. Once the balloon is positioned at the narrowed portion of the vessel to be treated, the balloon is expanded by pumping saline through the catheter to the balloon. The balloon then simultaneously dilates the vessel and radially expands the stent within the dilated portion. The balloon is then deflated and the balloon-tipped catheter is retracted from the passageway. This leaves the expanded stent permanently implanted at the desired location. Ductile metal lends itself to this type of stent since the stent may be compressed by plastic deformation to a small diameter when mounted onto the balloon. When the balloon is later expanded in the vessel, the stent once again plastically deforms to a larger diameter to provide the desired radial support structure. Traditionally, balloon-expandable stents have been more commonly used in coronary vessels than in peripheral vessels because of the deformable nature of these stents. In the case of coronary vessels, however, this is generally not a concern since coronary vessels rarely experience traumas transmitted from external sources. In addition, one advantage of balloon-expandable stents is that the expanded diameter of the stent may be precisely controlled during implantation. This is possible because the pressure applied to the balloon may be controlled by the physician to produce a precise amount of radial expansion and plastic deformation of the stent. In addition, balloons with a repeatable diameter for various pressures are typically used.

Stents may also be used in combination with other components to treat a number of medical conditions. For example, stent-graft assemblies are commonly used in the treatment of aneurysms. As those in the art well know, an aneurysm is an abnormal widening or ballooning of a portion of an artery. Generally, this condition is caused by a weakness in the blood vessel wall. High blood pressure and atherosclerotic disease may also contribute to the formation of aneurysms. Common types of aneurysms include aortic aneurysms, cerebral aneurysms, popliteal artery aneurysms, mesenteric artery aneurysms, and splenic artery aneurysms. However, it is also possible for aneurysms to form in blood vessels throughout the vasculature. If not treated, an aneurysm may eventually rupture, resulting in internal hemorrhaging. In many cases, the internal bleeding may be so massive that a patient might die within minutes of an aneurysm rupture. For example, in the case of aortic aneurysms, the survival rate after a rupture can be as low as 20%.

Traditionally, aneurysms have been treated with surgery. For example, in the case of an abdominal aortic aneurysm, the abdomen is surgically opened and the widened section of the aorta is removed. The remaining ends of the aorta are then surgically reconnected. In certain situations the surgeon may choose to replace the excised section of the aorta with a graft material such as Dacron. In still other situations, the surgeon may put a clip on the blood vessel at the neck of the aneurysm between the aneurysm and the primary passageway of the vessel. The clip then prevents blood flow from the vessel from entering the aneurysm.

An alternative to traditional surgery is endovascular treatment of the blood vessel with a stent-graft. This alternative involves implanting a stent-graft in the blood vessel across the aneurysm using conventional catheter-based placement techniques. The stent-graft treats the aneurysm by sealing the wall of the blood vessel with a generally impermeable graft material. Thus, the aneurysm is sealed off and blood flow is kept within the primary passageway of the blood vessel. Increasingly, treatments using stent-grafts are becoming preferred since the procedure results in less trauma and a faster recuperation.

A drug or other bioactive component may also be added to stents to enhance the function of a stent in certain applications. For example, one problem that has been encountered with common stenting procedures is stenosis or restenosis. Stenosis may occur for a variety of reasons, such as the vessel wall collapsing or the growth of new cellular tissue. For example, stenosis may occur as the result of damage caused to the vessel lining during balloon expansion and vessel dilation. This may cause the intima layers of the vessel to attempt to grow new intimal tissue to repair the damage. The tendency of vessels to regrow new tissue is generally referred to as neointimal hyperplasia. In addition, the synthetic materials that are usually used in stents may also contribute to neointimal hyperplasia. This is caused by the body's tendency to grow new living tissues around and over newly implanted foreign objects. The effect of these responses may result in a narrowing or re-narrowing of the vessel (i.e., stenosis or restenosis). However, stenosis is not completely predictable and may occur either abruptly soon after the stenting procedure due to a collapse in the vessel or may occur slowly over a longer period of time for other reasons. In any event, stenosis may defeat the original purpose of the stenting procedure, which is normally to open a narrowed portion of a vessel and to maintain the patency of the vessel.

One approach that has been offered to address the problem of stenosis has been to coat stents with drugs that are designed to inhibit cellular growth. Although many such drugs are known, common examples of these types of drugs include Paclitaxel, Sirolimus and Everolimus. One technique for combining beneficial drugs with an intraluminal device involves coating the drug directly onto the outer surfaces of the device. Alternatively, various pits or reservoirs may be designed into the intraluminal device to receive the drug. Common coating processes include dipping, spraying or painting the desired drug onto the intraluminal device. However, these are only some of the ways that a drug or other bioactive component may be used with a stent. Various other drugs and techniques may also be possible as well.

The above-described examples are only some of the applications in which stents are used by physicians. Many other applications for stents are known and/or may be developed in the future. Moreover, numerous other components may be added to a stent structure in addition to the graft materials and drug coatings described above.

SUMMARY

A delivery system is described with a stent mounted on the balloon of a balloon catheter. The stent is restrained on the balloon with a retention wire that extends the length of the stent and is positioned adjacent the outer surface of the stent. The retention wire is coupled to the catheter adjacent the distal end of the stent and adjacent the proximal end of the stent. The retention wire may be withdrawn after the balloon and stent have been expanded by passing the retention wire through a lumen that extends to the proximal end of the catheter. One advantage of the retention wire is that the stent is restrained from moving longitudinally during inflation of the balloon. As a result, the stent and balloon may not need to be heated and pressurized to the same extent currently done to couple stents onto a balloon. This may also have the advantage of reducing damage to various components that may be added to stents.

The invention may include any of the following aspects in various combinations and may also include any other aspect described below in the written description or in the attached drawings.

A delivery system for an endoluminal stent, comprising: a catheter comprising a balloon mounted on a distal end thereof, the catheter having a longitudinal lumen extending therethrough in fluid communication with an interior region of the balloon, the balloon thereby being expandable from a collapsed state to an expanded state;
a stent mounted on the balloon, the stent comprising a proximal end, a distal end and a length extending therebetween, an inner surface of the stent being disposed about an exterior region of the balloon, the stent initially being collapsed onto the balloon in the collapsed state, the stent being expandable in response to expansion of the balloon to the expanded state; and
a retention wire extending along the length of the stent and disposed adjacent an outer surface of the stent, the retention wire being coupled to the catheter adjacent the distal end of the stent, the wire being further coupled to the catheter adjacent the proximal end of the stent, the retention wire thereby restraining the stent from moving longitudinally relative the balloon.

The stent delivery system, wherein the retention wire is coupled to the catheter adjacent the distal end of the stent with a longitudinally extending distal lumen having a distal opening adjacent the distal end of the stent, the retention wire passing through the distal opening and a distal end of the retention wire being disposed within the distal lumen.

The stent delivery system, wherein the retention wire is restrained adjacent the distal end of the stent relative the catheter as the balloon is expanded, the retention wire being adapted to move relative the proximal end of the stent as the balloon is expanded.

The stent delivery system, wherein the distal lumen is a blind lumen in a distal end of the catheter.

The stent delivery system, wherein the distal lumen comprises first and second opposing surfaces, portions of the first and second surfaces being juxtaposed, the retention wire thereby being deformed by the first and second surfaces.

The stent delivery system, wherein the retention wire is deformed within an elastic range of the retention wire, the retention wire thereby returning to a generally straight configuration when withdrawn from the distal lumen.

The stent delivery system, wherein the retention wire is made from nitinol.

The stent delivery system, wherein the retention wire is coupled to the catheter adjacent the distal end of the stent with a spherical end formed at a distal end of the retention wire, the spherical end being retained within a socket molded into the catheter.

The stent delivery system, wherein the retention wire is coupled to the catheter adjacent the distal end of the stent with a longitudinally extending distal lumen having a distal opening adjacent the distal end of the stent, the retention wire passing through the distal opening and a distal end of the retention wire being disposed within the distal lumen, a length of the retention wire disposed within the distal lumen being longer than a stretch length caused by inflation of the balloon from the collapsed state to the expanded state, wherein the retention wire is restrained adjacent the proximal end of the stent relative the catheter as the balloon is expanded, the stretch length thereby being taken up at the distal opening and the retention wire remaining partially disposed within the distal lumen after the balloon is expanded to the expanded state.

The stent delivery system, wherein the retention wire is coupled to the catheter adjacent the distal end of the stent with a distal end of the retention wire molded into the catheter.

The stent delivery system, wherein the retention wire is coupled to the catheter adjacent the proximal end of the stent with a longitudinally extending proximal lumen having a proximal opening adjacent the proximal end of the stent, the retention wire passing through the proximal opening and extending to a proximal end of the catheter, a proximal end of the retention wire thereby being actuable to withdraw the retention wire away from the stent after the balloon is expanded to the expanded state.

The stent delivery system, wherein the retention wire is restrained adjacent the distal end of the stent relative the catheter as the balloon is expanded, the retention wire being adapted to move relative the proximal end of the stent as the balloon is expanded.

The stent delivery system, wherein the retention wire is tapered with a portion of the retention wire adjacent the distal end of the stent having a smaller cross sectional area than another portion of the retention wire adjacent the proximal end of the stent.

The stent delivery system, wherein the retention wire is tapered with a portion of the retention wire adjacent the distal end of the stent having a smaller cross sectional area than another portion of the retention wire adjacent the proximal end of the stent.

The stent delivery system, wherein the retention wire is a flat wire.

The stent delivery system, wherein the retention wire is coupled to the catheter adjacent the distal end of the stent with a longitudinally extending distal lumen having a distal opening adjacent the distal end of the stent, the retention wire passing through the distal opening and a distal end of the retention wire being disposed within the distal lumen, the distal lumen being a blind lumen in a distal end of the catheter, wherein the distal lumen comprises first and second opposing surfaces, portions of the first and second surfaces being juxtaposed, the retention wire thereby being deformed by the first and second surfaces, the retention wire being deformed within an elastic range of the retention wire, wherein the retention wire returns to a generally straight configuration when withdrawn from the distal lumen, the retention wire is made from nitinol, and wherein the retention wire is coupled to the catheter adjacent the proximal end of the stent with a longitudinally extending proximal lumen having a proximal opening adjacent the proximal end of the stent, the retention wire passing through the proximal opening and extending to a proximal end of the catheter, a proximal end of the retention wire thereby being actuable to withdraw the retention wire away from the stent after the balloon is expanded to the expanded state.

The stent delivery system, wherein the retention wire is coupled to the catheter adjacent the distal end of the stent with a longitudinally extending distal lumen having a distal opening adjacent the distal end of the stent, the retention wire passing through the distal opening and a distal end of the retention wire being disposed within the distal lumen, a length of the retention wire disposed within the distal lumen being longer than a stretch length caused by inflation of the balloon from the collapsed state to the expanded state, wherein the retention wire is restrained adjacent the proximal end of the stent relative the catheter as the balloon is expanded, the stretch length thereby being taken up at the distal opening and the retention wire remaining partially disposed within the distal lumen after the balloon is expanded to the expanded state, and wherein the retention wire is coupled to the catheter adjacent the proximal end of the stent with a longitudinally extending proximal lumen having a proximal opening adjacent the proximal end of the stent, the retention wire passing through the proximal opening and extending to a proximal end of the catheter, a proximal end of the retention wire thereby being actuable to withdraw the retention wire away from the stent after the balloon is expanded to the expanded state.

The stent delivery system, wherein the retention wire is tapered with a portion of the retention wire adjacent the distal end of the stent having a smaller cross sectional area than another portion of the retention wire adjacent the proximal end of the stent.

A delivery system for an endoluminal stent, comprising:
a catheter comprising a balloon mounted on a distal end thereof, the catheter having a longitudinal lumen extending therethrough in fluid communication with an interior region of the balloon, the balloon thereby being expandable from a collapsed state to an expanded state;
a stent mounted on the balloon, the stent comprising a proximal end, a distal end and a length extending therebetween, an inner surface of the stent being disposed about an exterior region of the balloon, the stent initially being collapsed onto the balloon in the collapsed state, the stent being expandable in response to expansion of the balloon to the expanded state;
a retention wire extending along the length of the stent and disposed adjacent an outer surface of the stent, the retention wire being coupled to the catheter adjacent the distal end of the stent, the wire being further coupled to the catheter adjacent the proximal end of the stent, the retention wire thereby restraining the stent from moving longitudinally relative the balloon;
wherein the retention wire is coupled to the catheter adjacent the distal end of the stent with a longitudinally extending distal lumen having a distal opening adjacent the distal end of the stent, the retention wire passing through the distal opening and a distal end of the retention wire being disposed within the distal lumen, the distal lumen being a blind lumen in a distal end of the catheter, wherein the distal lumen comprises first and second opposing surfaces, portions of the first and second surfaces being juxtaposed, the retention wire thereby being deformed by the first and second surfaces, the retention wire being deformed within an elastic range of the retention wire, wherein the retention wire returns to a generally straight configuration when withdrawn from the distal lumen, the retention wire is made from nitinol; and wherein the retention wire is coupled to the catheter adjacent the proximal end of the stent with a longitudinally extending proximal lumen having a proximal opening adjacent the proximal end of the stent, the retention wire passing through the proximal opening and extending to a proximal end of the catheter, a proximal end of the retention wire thereby being actuable to withdraw the retention wire away from the stent after the balloon is expanded to the expanded state.

A delivery system for an endoluminal stent, comprising:

a catheter comprising a balloon mounted on a distal end thereof, the catheter having a longitudinal lumen extending therethrough in fluid communication with an interior region of the balloon, the balloon thereby being expandable from a collapsed state to an expanded state;

a stent mounted on the balloon, the stent comprising a proximal end, a distal end and a length extending therebetween, an inner surface of the stent being disposed about an exterior region of the balloon, the stent initially being collapsed onto the balloon in the collapsed state, the stent being expandable in response to expansion of the balloon to the expanded state;

a retention wire extending along the length of the stent and disposed adjacent an outer surface of the stent, the retention wire being coupled to the catheter adjacent the distal end of the stent, the wire being further coupled to the catheter adjacent the proximal end of the stent, the retention wire thereby restraining the stent from moving longitudinally relative the balloon;

wherein the retention wire is coupled to the catheter adjacent the distal end of the stent with a longitudinally extending distal lumen having a distal opening adjacent the distal end of the stent, the retention wire passing through the distal opening and a distal end of the retention wire being disposed within the distal lumen, a length of the retention wire disposed within the distal lumen being longer than a stretch length caused by inflation of the balloon from the collapsed state to the expanded state, wherein the retention wire is restrained adjacent the proximal end of the stent relative the catheter as the balloon is expanded, the stretch length thereby being taken up at the distal opening and the retention wire remaining partially disposed within the distal lumen after the balloon is expanded to the expanded state; and wherein the retention wire is coupled to the catheter adjacent the proximal end of the stent with a longitudinally extending proximal lumen having a proximal opening adjacent the proximal end of the stent, the retention wire passing through the proximal opening and extending to a proximal end of the catheter, a proximal end of the retention wire thereby being actuable to withdraw the retention wire away from the stent after the balloon is expanded to the expanded state.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
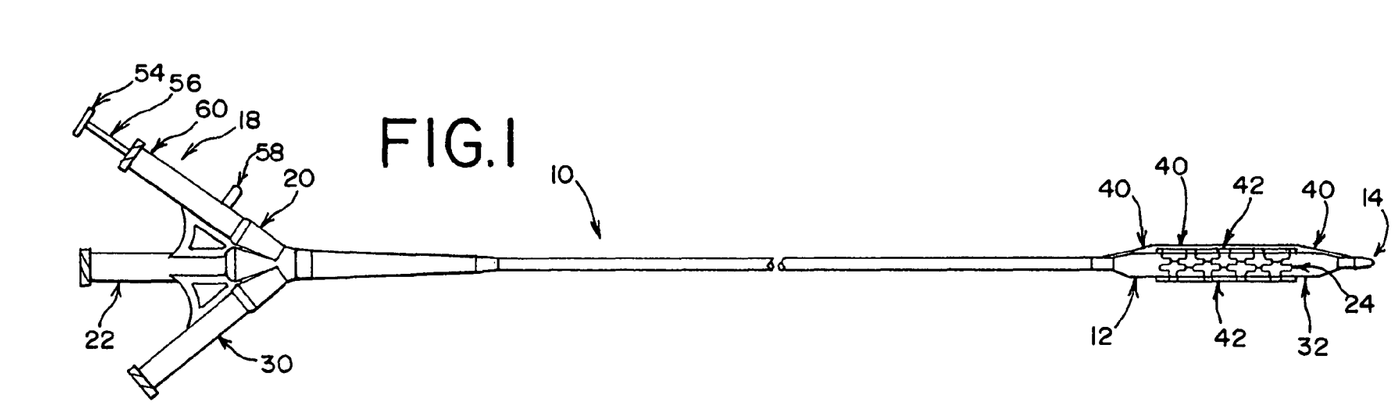
FIG. 1 is a side elevational view of a balloon catheter with a stent mounted thereon.

Referring now to the drawings, and particularly to FIG. 1, an intraluminal catheter 10 is shown. The catheter 10 has a balloon 12 mounted near the distal end 14 of the catheter 10. A guidewire lumen 16 (shown in FIGS. 3-6) may be provided which extends from the distal end 14 of the catheter 10 to the proximal end 18 of the catheter 10. A manifold 20 is also provided at the proximal end 18 of the catheter 10. One of the ports 22 of the manifold 20 may be used to pass a guidewire through the guidewire lumen 16. A balloon-expandable stent 24 may be mounted on the balloon 12 for endoluminal implantation within a patient's body. As shown in FIG. 1, the balloon 12 is illustrated in a collapsed state. In the collapsed state, the stent 24 is crimped onto the balloon 12 in a low profile, small diameter that is suitable for passage through narrow arteries and other passageways.

Figure 2:
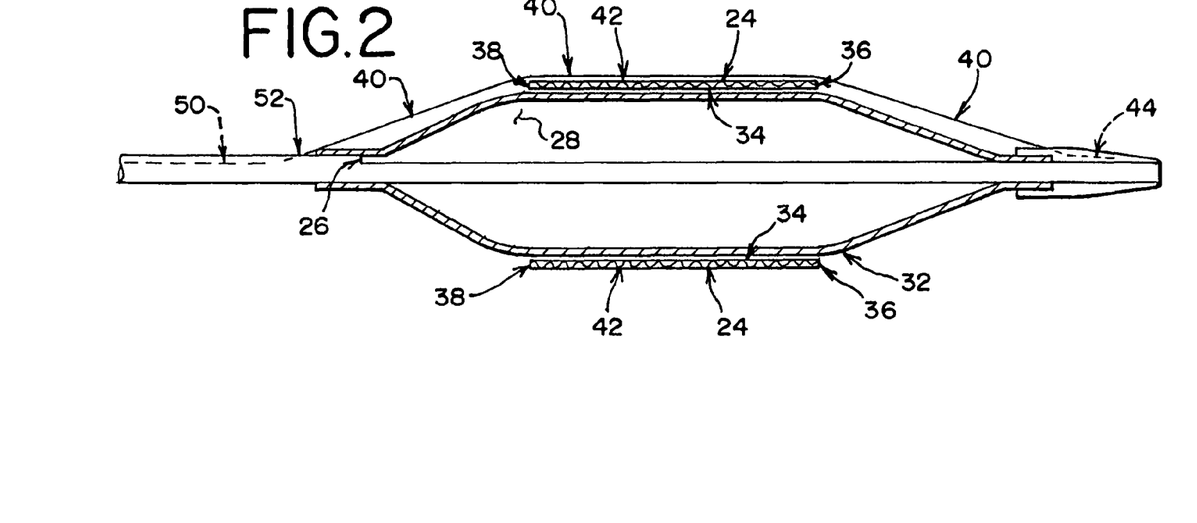
FIG. 2 is a partial cross sectional view of the balloon catheter in an expanded state.

As shown in FIG. 2, the balloon 12 is illustrated in an expanded state. The balloon 12 is expandable by passing fluid through a lumen 26 which extends longitudinally from the proximal end 18 of the catheter 10 to the interior region 28 of the balloon 12. As shown in FIG. 1, the pressurized fluid may be supplied to the inflation lumen 26 and the interior region 28 of the balloon 12 through a port 30 on the manifold 20. Thus, as the balloon 12 is expanded, the engagement between the exterior region 32 of the balloon 12 and the inner surface 34 of the stent 24 causes the stent 24 to expand.

One of the problems that may be experienced with conventional balloon expandable stent delivery systems is an unintended longitudinal movement of the stent relative to the balloon. This problem may be of particular concern during balloon inflation, but problems of this nature may also occur during positioning of a catheter or other procedures. As shown in FIG. 2, the stent 24 is typically mounted about the longitudinal center of the balloon 12 so that the distal end 36 of the stent 24 and the proximal end 38 of the stent 24 are spaced equally from the ends of the balloon 12. However, various off-center arrangements are also possible. Longitudinal movement of the stent during inflation may occur for a variety of reasons. For example, one problem is that conventional balloons do not always inflate equally during the inflation process along the length of the balloon. This can cause the stent to slide along the length of the balloon. This may be a particular problem with some balloons that use relatively stiff or low compliance materials for the balloon and high inflation pressures. Sliding of the stent may also be encouraged by balloons that have a slippery exterior surface. In addition, blood flow which typically surrounds the balloon and stent during implantation procedures may enhance the slipperiness of the stent and balloon.

One approach that has been used to prevent longitudinal movement of stents mounted on a balloon involves heat-setting the exterior region of the balloon to the inner surface of the stent. This process requires the stent to be restrained along the outer surface of the stent in the crimped, small diameter while mounted on the uninflated balloon. The restraint is designed to prevent the stent from expanding. The assembly may then be heated and inflation pressure applied to the balloon. This causes the balloon to remold slightly to conform to the inner structure of the stent. Once the inflation pressure is released and the temperature returns to ambient, the balloon retains the slightly conformed shape. As a result, some amount of physical engagement between the balloon and the stent occurs. While this approach has proven to be acceptable under certain circumstances, there may be situations where this approach is less preferred. One concern is that the pressure and temperature that must be applied to the balloon and stent assembly may adversely affect some of the components of the assembly. For example, in a typical process utilizing the approach described above, the balloon and stent may be heated to about 150° C. and a pressure of about 200 psi (15 bar) may be applied to the balloon. This may have the potential to damage various drug coatings that may be applied to a stent or biologic components attached to the stent or numerous other coatings, graft layers, attached components and the like.

As shown in FIGS. 1 and 2, one solution to these problems is a retention wire 40 used to restrain the stent 24 on the balloon 12. One advantage of the retention wire 40 is that the stent 24 may be restrained on the balloon 12 during inflation and at other times without requiring the balloon 12 and stent 24 to be heated and pressurized as described above to conform the balloon 12 to the stent 24. Alternatively, less heat and pressure may be used to prevent damage to coatings or other components while providing a small amount of coupling between the balloon 12 and the stent 24.

The retention wire 40 extends along the length of the stent 24 adjacent the outer surface 42 of the stent 24. The retention wire 40 is coupled to the catheter 10 adjacent the distal end 36 of the stent 24 and is coupled to the proximal end 38 of the stent 24. Preferably, the retention wire 40 is restrained at either the proximal end 18 of the catheter 10 or the distal end 14 of the catheter 10 and pulled tight so that the wire 40 comes into contact with the outer surface 42 of the stent 24. As shown in FIG. 2, when the balloon 12 is inflated, the retention wire 40 moves outward with the stent 24 to accommodate the stretch length caused by inflation of the balloon 12 from its collapsed state to the expanded state. The stretch length that occurs during inflation may be accommodated in several ways as described below and shown in FIGS. 4-6.

Figure 3:
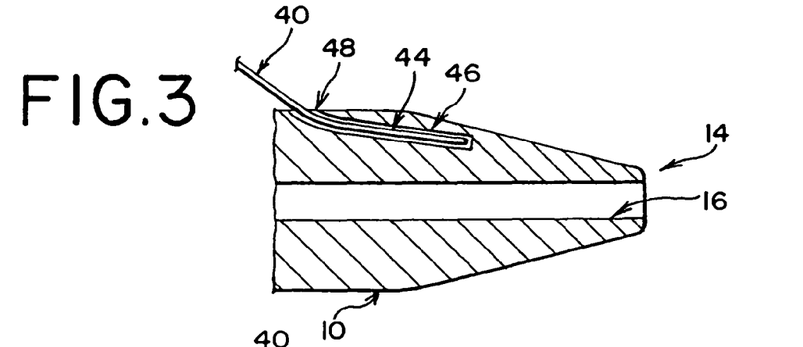
FIG. 3 is an enlarged cross sectional view of the distal end of the balloon catheter, showing one embodiment for coupling a distal end of a retention wire thereto.

As shown in FIG. 3, the distal end 44 of the retention wire 40 may be disposed within a distal lumen 46 that extends longitudinally through the distal end 14 of the catheter 10. The distal lumen 46 includes a distal opening 48 facing toward the stent 24 and positioned adjacent the distal end 36 of the stent 24. Preferably, the distal lumen 46 is a blind lumen that does not have an opening facing toward the distal end 14 of the catheter 10. The retention wire 40 extends to the proximal end 18 of the catheter 10 by passing through a longitudinally extending proximal lumen 50 having a proximal opening 52 adjacent the proximal end 38 of the stent 24. A handle 54 or other structure may be provided at the proximal end 56 of the retention wire 40 to allow the physician to actuate the retention wire 40 to withdraw it. The retention wire 40 may be restrained at the proximal end 38 of the stent 24 with a locking member 58 secured to the retention wire port 60 of the manifold 20. Thus, the locking member 58 locks the proximal end 56 of the retention wire 40 to the manifold 20. As a result, when the balloon 12 is inflated as shown in FIG. 2, the stretch length caused by the inflation is taken up at the distal opening 48 of the distal lumen 46. Specifically, the retention wire 40 is partially withdrawn from the distal lumen 46 during inflation to accommodate the stretch caused by balloon inflation. However, the length of the distal lumen 46 and the retention wire 40 are preferably long enough so that the retention wire 40 remains partially disposed within the distal lumen 46 after the balloon 12 is fully inflated. Once the balloon 12 is inflated and the stent 24 implanted, the retention wire 40 may be removed by unsecuring the locking member 58 and withdrawing the retention wire 40 through the manifold 20. During withdrawal, the retention wire 40 passes between the vessel wall and the outer surface 42 of the stent 24.

If desired, the retention wire 40 may be made from a tapered wire to ease passage between the stent 24 and the vessel wall. For example, the cross-sectional area of the retention wire 40 may be 0.008" adjacent the proximal end 38 of the stent 24 and 0.003" adjacent the distal end 36 of the stent 24. However the retention wire 40 may also have a generally constant diameter of about 0.008". Alternatively, the retention wire 40 may be made from a flat wire 0.008" wide and 0.003" thick, where the width of the flat wire is adjacent the outer surface 42 of the stent 24 and the thickness of the flat wire extends between the stent 24 and the vessel wall. The retention wire 40 may also be made from various materials. For example, the retention wire 40 may be made from conventional metals like stainless steel. The retention wire 40 may also be made from nitinol or various polymers.

Figures 4, 5:
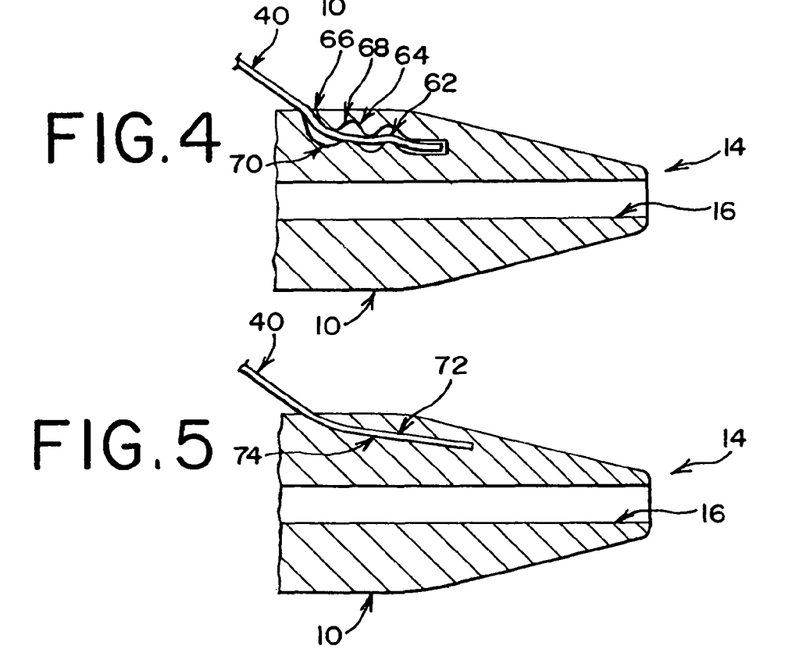
FIG. 4 is an enlarged cross sectional view of the distal end of the balloon catheter, showing another embodiment for coupling the distal end of the retention wire thereto.
FIG. 5 is an enlarged cross sectional view of the distal end of the balloon catheter, showing another embodiment for coupling the distal end of the retention wire thereto.

In FIG. 4, another arrangement for coupling the distal end 62 of the retention wire 40 to the catheter 10 is shown. As shown, the distal end 62 of the retention wire 40 may be disposed within a distal lumen 64 extending longitudinally through the distal end 14 of the catheter 10. The distal lumen 64 includes a distal opening 66 facing toward the stent 24 and positioned adjacent the distal end 36 of the stent 24. The distal lumen 64 includes opposing first and second surfaces 68, 70 that are juxtaposed with each other so that the distal end 62 of the retention wire 40 is partially deformed. Preferably, the deformation of the distal end 62 of the retention wire 40 is within the elastic range of the material used for the wire 40 so that the retention wire 40 straightens when withdrawn from the distal lumen 64. One preferred material to prevent permanent deformation of the retention wire 40 is nitinol. Because the retention wire 40 is restrained at the distal end 36 of the stent 24 in this configuration, the locking member 58 is preferably not used during inflation of the balloon 12. As a result, the proximal end 56 of the retention wire 40 may move relative to the catheter 10 during balloon inflation to take up the stretch caused by the balloon 12. After the balloon 12 is inflated, the retention wire 40 may be removed by pulling on the retention wire handle 54 at the proximal end 56 of the retention wire 40. This forces the distal end 62 of the retention wire 40 to disengage from the first and second surfaces 68, 70 of the distal lumen 64. The retention wire 40 may then be withdrawn by passing the retention wire 40 between the outer surface 42 of the stent 24 and the vessel wall.

In FIG. 5, another arrangement for coupling the distal end 72 of the retention wire 40 is shown. In this configuration, the distal end 72 of the retention wire 40 is molded 74 into the catheter 10. As a result, the retention wire 40 is restrained adjacent the distal end 36 of the stent 24. This embodiment may be used in a similar manner as the embodiment shown in FIG. 4. Thus, to withdraw the retention wire 40, the handle 54 at the proximal end 56 of the retention wire 40 is pulled after the balloon 12 has been inflated. This causes the distal end 72 of the retention wire 40 to disengage from the distal end 14 of the catheter 10. In order to make disengagement of the distal end 72 of the retention wire 40 easier, the retention wire 40 may be tapered within the molded-in portion 74. The retention wire 40 is withdrawn as described above by passing the retention wire 40 between the outer surface 42 of the stent 24 and the vessel wall.

Figure 6:
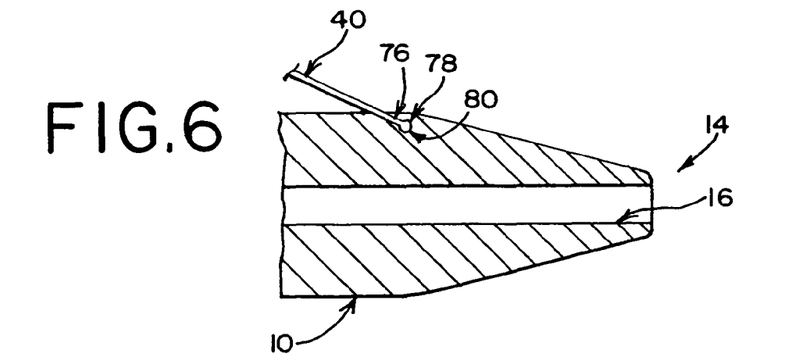
FIG. 6 is an enlarged cross sectional view of the distal end of the balloon catheter, showing another embodiment for coupling the distal end of the retention wire thereto.

In FIG. 6, still another arrangement for coupling the distal end 76 of the retention wire 40 is shown. In this configuration, a spherical end 78 is formed at the distal end 76 of the retention wire 40. The spherical end 78 is received by a socket 80 molded into the catheter 10. Thus, the socket 80 restrains the retention wire 40 adjacent the distal end 36 of the stent 24. This embodiment may be used in a similar manner as the embodiment shown in FIG. 5. To withdraw the retention wire 40, the handle 54 at the proximal end 56 of the retention wire 40 may be pulled after the balloon 12 has been inflated. This causes the spherical end 78 of the retention wire 40 to disengage from the socket 80. The retention wire 40 is then withdrawn by passing the retention wire 40 between the outer surface 42 of the stent 24 and the vessel wall.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A delivery system for an endoluminal stent, comprising:
   a catheter comprising a balloon mounted on a distal end thereof, said catheter having a longitudinal lumen extending therethrough in fluid communication with an interior region of said balloon, said balloon thereby being expandable from a collapsed state to an expanded state;
   a balloon-expandable stent mounted on said balloon, said stent comprising a proximal end, a distal end and a length extending therebetween, an inner surface of said stent being disposed about an exterior region of said balloon, said stent initially being collapsed onto said balloon in said collapsed state, said stent being expandable in response to expansion of said balloon to said expanded state; and
   a single retention wire extending over a proximal end of said stent and along only an external surface thereof for an entirety of said length of said stent, said retention wire further extending over said distal end of said stent such that said retention wire is free of attachment to said stent, wherein said retention wire is coupled to said catheter adjacent said distal end of said stent, and said retention wire is further coupled to said catheter adjacent said proximal end of said stent, said retention wire extending along a generally straight direction between said proximal and distal ends thereby restraining said stent from moving longitudinally relative said balloon.

2. The stent delivery system according to claim 1, wherein said retention wire is coupled to said catheter adjacent said distal end of said stent with a longitudinally extending distal lumen having a distal opening adjacent said distal end of said stent, said retention wire passing through said distal opening and a distal end of said retention wire being disposed within said distal lumen.

3. The stent delivery system according to claim 2, wherein said retention wire is restrained adjacent said distal end of said stent relative said catheter as said balloon is expanded, said retention wire moving relative to said proximal end of said stent as said balloon is expanded.

4. The stent delivery system according to claim 2, wherein said distal lumen is a blind lumen in a distal end of said catheter.

5. The stent delivery system according to claim 2, wherein said distal lumen comprises first and second opposing surfaces, portions of said first and second surfaces being juxtaposed, said retention wire thereby being deformed by said first and second surfaces.

6. The stent delivery system according to claim 5, wherein said retention wire is deformed within an elastic range of said retention wire, said retention wire thereby returning to a generally straight configuration when withdrawn from said distal lumen.

7. The stent delivery system according to claim 6, wherein said retention wire is made from nitinol.

8. The stent delivery system according to claim 1, wherein said retention wire is coupled to said catheter adjacent said distal end of said stent with a spherical end formed at a distal end of said retention wire, said spherical end being retained within a socket molded into said catheter.

9. The stent delivery system according to claim 1, wherein said retention wire is coupled to said catheter adjacent said distal end of said stent with a longitudinally extending distal lumen having a distal opening adjacent said distal end of said stent, said retention wire passing through said distal opening and a distal end of said retention wire being disposed within said distal lumen, a length of said retention wire disposed within said distal lumen being longer than a stretch length caused by inflation of said balloon from said collapsed state to said expanded state, wherein said retention wire is restrained adjacent said proximal end of said stent relative said catheter as said balloon is expanded, said stretch length thereby being taken up at said distal opening and said retention wire remaining partially disposed within said distal lumen after said balloon is expanded to said expanded state.

10. The stent delivery system according to claim 1, wherein said retention wire is coupled to said catheter adjacent said distal end of said stent with a distal end of said retention wire molded into said catheter.

11. The stent delivery system according to claim 1, wherein said retention wire is coupled to said catheter adjacent said proximal end of said stent with a longitudinally extending proximal lumen having a proximal opening adjacent said proximal end of said stent, said retention wire passing through said proximal opening and extending to a proximal end of said catheter, wherein after said balloon is expanded to said expanded state, said stent is released by withdrawing a proximal end of said retention wire in a proximal direction.

12. The stent delivery system according to claim 11, wherein said retention wire is restrained adjacent said distal end of said stent relative said catheter as said balloon is expanded, and wherein as said balloon is expanded, said retention wire is moved relative to said proximal end of said stent.

13. The stent delivery system according to claim 12, wherein said retention wire is tapered with a portion of said retention wire adjacent said distal end of said stent having a smaller cross sectional area than another portion of said retention wire adjacent said proximal end of said stent.

14. The stent delivery system according to claim 1, wherein said retention wire is tapered with a portion of said retention wire adjacent said distal end of said stent having a smaller cross sectional area than another portion of said retention wire adjacent said proximal end of said stent.

15. The stent delivery system according to claim 1, wherein said retention wire is a flat wire.

16. The stent delivery system according to claim 1, wherein said retention wire is coupled to said catheter adjacent said distal end of said stent with a longitudinally extending distal lumen having a distal opening adjacent said distal end of said stent, said retention wire passing through said distal opening and a distal end of said retention wire being disposed within said distal lumen, said distal lumen being a blind lumen in a distal end of said catheter, wherein said distal lumen comprises first and second opposing surfaces, portions of said first and second surfaces being juxtaposed, said retention wire thereby being deformed by said first and second surfaces, said retention wire being deformed within an elastic range of said retention wire, wherein said retention wire returns to a generally straight configuration when withdrawn from said distal lumen, said retention wire is made from nitinol, and wherein said retention wire is coupled to said catheter adjacent said proximal end of said stent with a longitudinally extending proximal lumen having a proximal opening adjacent said proximal end of said stent, said retention wire passing through said proximal opening and extending to a proximal end of said catheter, wherein after said balloon is expanded to said expanded state, said stent is released by withdrawing a proximal end of said retention wire in a proximal direction.

17. The stent delivery system according to claim 1, wherein said retention wire is coupled to said catheter adjacent said distal end of said stent with a longitudinally extending distal lumen having a distal opening adjacent said distal end of said stent, said retention wire passing through said distal opening and a distal end of said retention wire being disposed within said distal lumen, a length of said retention wire disposed within said distal lumen being longer than a stretch length caused by inflation of said balloon from said collapsed state to said expanded state, wherein said retention wire is restrained adjacent said proximal end of said stent relative said catheter as said balloon is expanded, said stretch length thereby being taken up at said distal opening and said retention wire remaining partially disposed within said distal lumen after said balloon is expanded to said expanded state, and wherein said retention wire is coupled to said catheter adjacent said proximal end of said stent with a longitudinally extending proximal lumen having a proximal opening adjacent said proximal end of said stent, said retention wire passing through said proximal opening and extending to a proximal end of said catheter, wherein after said balloon is expanded to said expanded state, said stent is released by withdrawing a proximal end of said retention wire in a proximal direction.

18. The stent delivery system according to claim 17, wherein said retention wire is tapered with a portion of said retention wire adjacent said distal end of said stent having a smaller cross sectional area than another portion of said retention wire adjacent said proximal end of said stent.

* * * * *

UNITED STATES PATENT AND TRADEMARK OFFICE
CERTIFICATE OF CORRECTION

| | | |
|---|---|---|
| PATENT NO. | : 8,414,633 B2 | Page 1 of 1 |
| APPLICATION NO. | : 11/488331 | |
| DATED | : April 9, 2013 | |
| INVENTOR(S) | : Sisken | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,930 days.

Signed and Sealed this
Nineteenth Day of November, 2013

Teresa Stanek Rea
*Deputy Director of the United States Patent and Trademark Office*